United States Patent [19]

Smythe et al.

[11] 4,253,846

[45] Mar. 3, 1981

[54] METHOD AND APPARATUS FOR AUTOMATED ANALYSIS OF FLUID SAMPLES

[75] Inventors: William J. Smythe, Canterbury, Conn.; Jack Isreeli, Mamaroneck; Milton H. Pelavin, Chappaqua, both of N.Y.

[73] Assignee: Technicon Instruments Corporation, Tarrytown, N.Y.

[21] Appl. No.: 96,703

[22] Filed: Nov. 21, 1979

[51] Int. Cl.³ .................. G01N 1/14; G01N 35/08
[52] U.S. Cl. .................................. 23/230 R; 422/82; 23/230 B
[58] Field of Search ................. 23/230 R, 230 B; 422/81, 82

[56] References Cited

U.S. PATENT DOCUMENTS

| | | | |
|---|---|---|---|
| 3,600,953 | 8/1971 | Isreeli et al. | 422/82 X |
| 3,921,439 | 11/1975 | Burns | 422/82 X |
| 4,009,999 | 3/1977 | Negersmith | 23/230 R |
| 4,049,381 | 9/1977 | Burns et al. | 23/230 R |
| 4,130,394 | 12/1978 | Negersmith | 422/82 X |

Primary Examiner—R. E. Serwin
Attorney, Agent, or Firm—S. P. Tedesco

[57] ABSTRACT

A sample analyzing system features a number of discrete sample segments continuously conveyed along a conduit. Each sample segment receives a precise aliquot of one or more reagents on a selective basis, and in any particular sequence. Selective injection of the reagent into the moving stream of sample segments allows for an increase in the efficiency and throughput of the sample processing.

31 Claims, 6 Drawing Figures

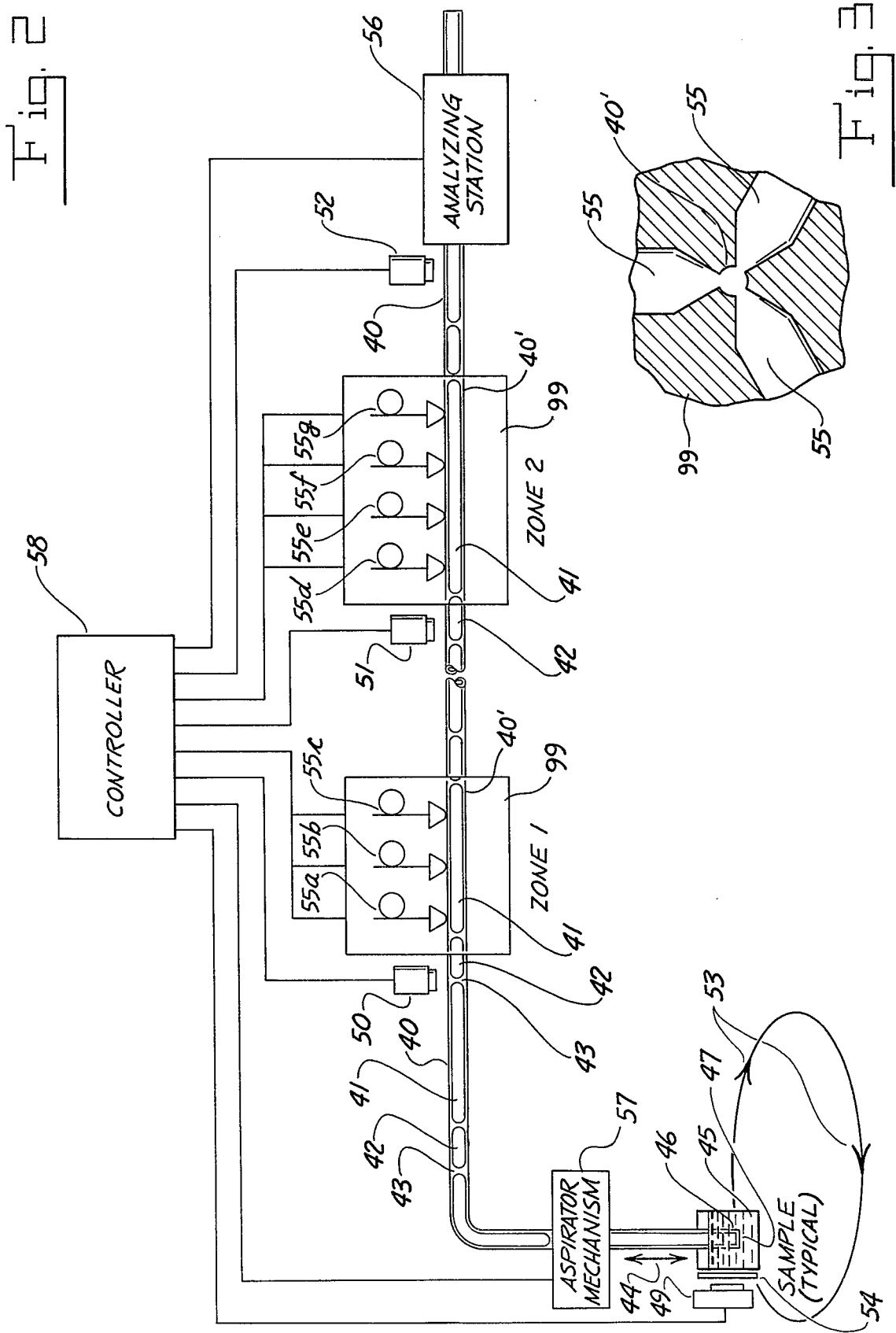

METHOD AND APPARATUS FOR AUTOMATED ANALYSIS OF FLUID SAMPLES

FIELD OF THE INVENTION

The invention relates to an analyzing system for determing one or more analytes in successive fluid samples flowing as a continuous stream through a conduit and, more particularly, to method and apparatuses for introducing precise aliquots of reagents into discrete segments of the fluid samples in any particular sequence to provide a greater efficiency and throughput of the sample processing.

BACKGROUND OF THE INVENTION

Continuous-flow systems of the type shown in the L. T. Skeggs, U.S. Pat. No. 3,241,432, issued on Mar. 22, 1966, and assigned to a common assignee, provide for the quantitative analysis of biological samples. Such systems generally contemplate passing a plurality of liquid segments successively as a continuous stream along a conduit, each sample segment being segmented and interdigitated by air or other inert fluid segments. Such segmentation pattern assists in intramixing the individual sample segments and maintains a uniform flow pattern. The air segments reduce contamination between successive sample segments by preventing carryover, i.e., contamination of successive sample segments by residues from a preceding sample segment remaining on the conduit wall. The air segments serve to scrub the walls of the conduit clean of these residues, so as to reduce carryover. In addition, a wash liquid segment is introduced between successive sample segments, so as to further reduce the possibility of contamination therebetween.

In prior art continuous-flow systems, introduction of diluent and/or reagents to the sample stream is generally achieved by the confluence of the sample stream with a continuously flowing diluent and/or reagent stream. As a result, reagent and/or diluent are introduced into portions of the continuous stream other than the sample segments and, hence, are wasted. In addition, the presence of many segments of both air, wash liquid and sample increases the processing time of the successive samples. Also, the basic operability of these continuous-flow systems requires that each analyte in a sample be analyzed in a separate channel, i.e., a plurality of analytical channels is required for multiple analyte testing.

In addition, these prior systems do not completely eliminate residue carryover, and rely on the scrubbing action of the air segments to clean the conduit wall of the leftover reagent.

In the blood-typing systems shown in the Peoples et al, U.S. Pat. No. 3,635,680, issued on Jan. 18, 1972, and assigned to a common assignee, a system is shown for reducing reagent uptake or consumption by introducing segments of different reagents in phased fashion and in fixed sequence, so as to merge with different segments of a same sample flowing in a continuous stream. While the system substantially reduces reagent consumption, it does not fully eliminate residue carryover or provide selectivity in respect of the analysis to be performed on each sample, i.e., the same tests are performed for each sample even if not required or desired. Thus, there is much waste and inefficiency in the processing of samples in this system.

In the W. J. Smythe et al, U.S. Pat. No. 3,479,141, issued on Nov. 18, 1969, and assigned to a common assignee, a continuous-flow system is described wherein carryover between successive samples in a continuously flowing stream is effectively eliminated. This system features encapsulation of the sample and air segments within an immiscible fluid. The immiscible fluid preferentially wets the interior surfaces of the conduit walls to the exclusion of the aqueous samples, thus completely eliminating residue carryover between successive samples. Reagents, however, are introduced in conventional fashion.

The present invention finds particular application in systems such as described in above-identified Smythe et al patent, to minimize reagent consumption by injecting a multiplicity of reagents, in precise controlled volumes and in a selected sequence, to any number of different segments of a same sample flowing in a continuous stream. The ability to selectively inject controlled volumes of different reagents into discrete sample segments moving along a conduit substantially minimizes reagent consumption. In addition, the variable (random) sequencing of the reagent injection coupled with introducing only that number of segments of each sample required for the desired analyses thereof allows for substantial increase in system throughput.

SUMMARY OF THE INVENTION

The invention relates to a sample analyzing system and an automated method and apparatus for quantitatively determining different analytes present in a fluid sample. Each sample is introduced into such system as a number of discrete successive segments separated by air segments, such number being related to the number of analytes to be tested. In the preferred embodiment, an immiscible carrier fluid is introduced into the system which preferentially wets the conduit wall to the exclusion of the sample segments. In effect, the carrier fluid fully encapsulates each sample segment as it is passed along the system, so as to eliminate carryover. However, it is contemplated that the invention may likewise be practiced in a conventional continuous-flow system, for example, as described in the above-identified Skeggs et al patent. Each sample segment is transported through the system past a reagent injection station, wherein each discrete sample segment is selectively injected with one or more reagents.

Basically, the present invention comprises: a conduit defining a sample flow path; means for conveying a multiplicity of discrete sample segments along the flow path; means for introducing precise aliquots of reagents, on a selective basis, into said discrete sample segments; and means for analyzing said discrete sample segments.

The method by which the reagents are introduced to the sample segments comprises: flowing successive sample segments along a conduit, introducing a controlled quantity of a reagent into selected one of said segments during flow thereof along said conduit, and analyzing said selected segment. In the preferred embodiment, the reagent is introduced by piercing the immiscible fluid layer encapsulating the selected sample segments. The immiscible fluid layer reforms after injection to maintain sample integrity and prevent carryover between successive samples.

In the preferred embodiment of the invention, reagent injection is effected by a number of poppet valves disposed circumferentially or in close adjacency axially along a portion of the conduit. The poppet valve arrangement is designed to forcibly inject the reagent to be introduced into the sample segment under pressure, so as to pierce the immiscible fluid layer during passage along the conduit portion. The tip of the poppet valve is formed of a same material and, also, conforms to or defines a portion of the inner wall surface of the conduit when in a closed position, so as to facilitate the reformation of the pierced immiscible fluid layer about the sample segment and, also, to prevent carryover.

It is a main object of this invention to provide an improved sample analyzing system of the continuous-flow type;

It is an object of this invention to provide a sample analyzing system having reduced reagent consumption;

It is another object of this invention to provide a method and apparatuses for improving the throughout of a sample analyzing system;

It is a further object of this invention to provide improved method and apparatuses for injecting reagent and/or dilutent into select ones of a plurality of discrete sample segments being successively transported along a conduit;

It is a further object of this invention to provide a sample analyzing system which affords random selectively in respect of the analyses to be performed on successive samples;

It is a further object of this invention to provide a sample analyzing system which requires minimal sample requirements to effect the analyses of a plurality of analytes;

These and other objects of this invention will become more apparent and will be better understood with reference to the following detailed description taken in conjunction with the accompanying drawings.

BRIEF DESCRIPTION OF THE DRAWINGS

FIG. 2 is a schematic diagram of the continuous-flow analyzing system of this invention;

FIG. 3 is a sectional view of the reagent injectors of FIG. 2; and

DETAILED DESCRIPTION OF THE INVENTION

Figures 1, 4:
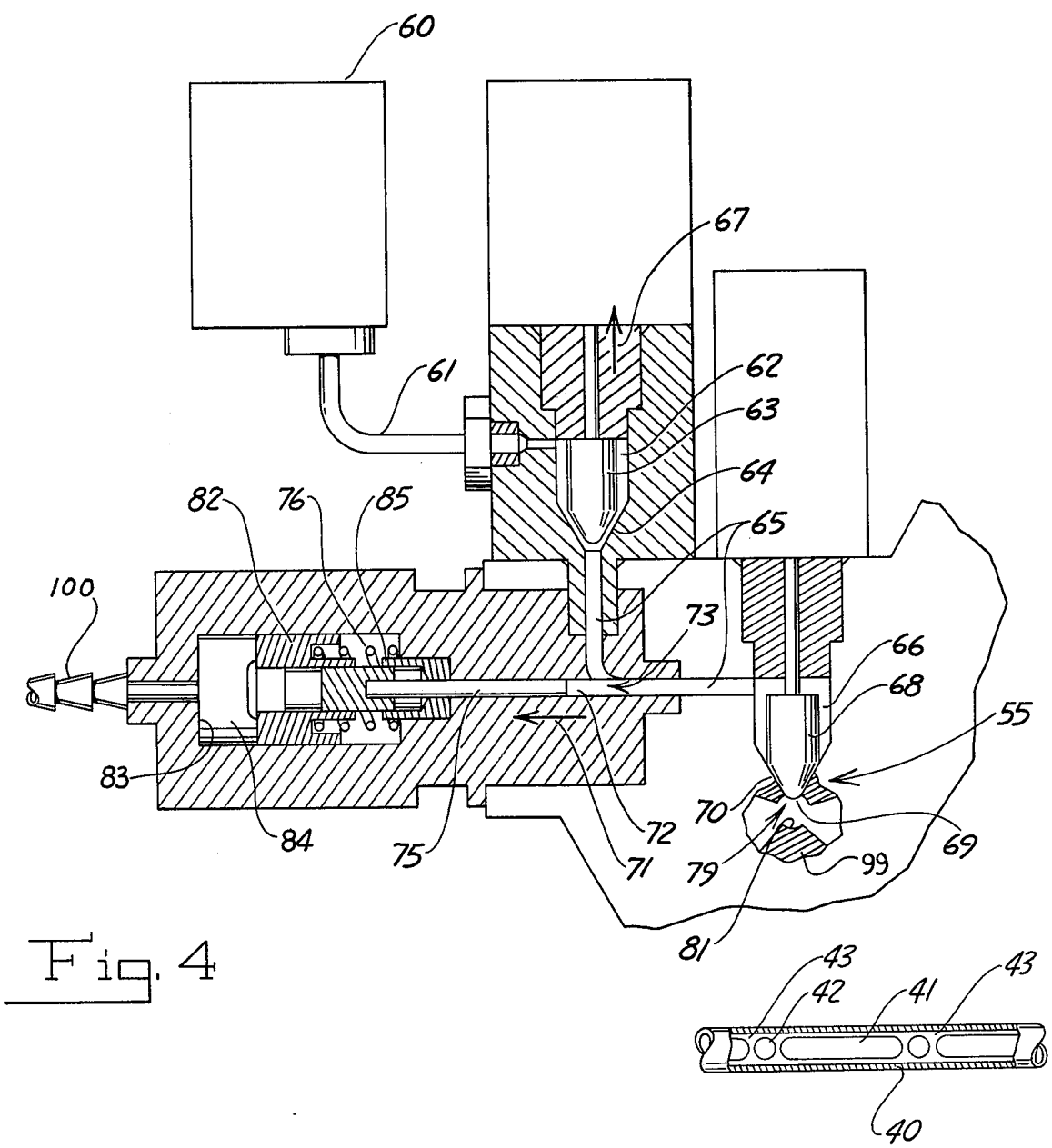
FIG. 1 is a schematic diagram of samples flowing along a continuous-flow analyzing system.
FIGS. 4 through 6 are schematic diagrams illustrating the operating sequence of the reagent injectors of FIG. 2.

The invention shown in FIG. 2 features a new analyzing system which minimizes reagent consumption and improves the processing or analyzing rate (throughput). Such system conveys a plurality of interdigitated sample segments 41 and air segments 42 as a continuous stream through a conduit 40. In a preferred embodiment, each segment is encapsulated within an immiscible carrier fluid 43, as additionally shown in the enlarged view of a section of conduit 40 illustrated in FIG. 1 and more fully described in the above-identified Smythe et al patent. The carrier fluid 43 is immiscible with the sample segments 41 and preferentially wets the inner wall surface of conduit 40, to prevent contamination between successive sample segments. The air segments 42 serve to maintain a proper flow pattern of the sample stream along conduit 40.

As there is no residue carryover between successive sample segments 41, each segment is available for an analysis and only one sample stream is needed for the testing of the many different analytes in the sample.

The system of FIG. 2 includes a controller 58 for controlling the selective injection of reagents into certain ones of the sample segments 41. This is accomplished by storing information upon individual sample entry, which information contains the desired analyses to be performed for each such sample, and then controlling the selective injection of the required reagents when the corresponding segments of each respective sample are passed to a reagent injection zone.

The controller 58 can be a general purpose digital computer with a stored (fixed) program. The peripherals can be a CRT display for instructing and informing the operator, a keyboard for receiving information, and a printer for recording the test data of each analysis (not shown). There are three types of memory in the system: ROM (non-volatile) storage; RAM (working data) storage and disc (mass, non-volatile) memory. The ROM memory contains the program for monitoring sample entry (aspiration of sample) and sample travel through the conduit 40. The monitored data is used to control the reagent injectors and analyzer station. The disc memory transfers delay parameters into working (RAM) memory for use in commanding the reagent injectors when the sample segments enter the reagent injection zones.

Because all the flow data received by the controller is on a sequential basis (detection of one segment after another), the data contained in disc memory has fixed parameters for injection times and analyzer control. Other memory allocations are, of course, possible in the context of this invention.

The controller 58 uses stored standard algorithms for converting optical data received from a colorimeter or other detecting device into analysis information, which information can appear on the display and/or can be delivered as hard-copy by the printer.

To effect sample entry, the system of FIG. 2 comprises a sample indexing tray (not shown) which rotates (arrows 53) or otherwise delivers each sample cup 45, in turn, beneath an aspirating probe 46.

Air and sample are alternately aspirated via a probe 46, which periodically dips into sample cup 45 (arrows 44). The immiscible fluid 43 is introduced to the inlet end 47 of the probe 46 by an applicator (not shown) and is aspirated along with air between successive "sample" immersions to form the illustrated flow pattern of FIG. 1. The indexing tray and aspirating probe system are more fully described in patent application Ser. No. 57,541, filed on July 13, 1979, which description is incorporated herein by reference.

Each sample cup 45 has a label 54 attached thereto. Label 54 contains a suitable code indicating the particular analyses to be performed on the sample. Label 54 is read by detector 49, which relates this information to the controller 58. The controller 58 stores this information and, at the appropriate time, will control the injection of the sample segments with the required reagents for the tests which are designated on label 54. The controller 58 also controls the aspirating mechanism 57, such that only the number of sample segments 41 equal to the number of analytes to be tested and interdigitated by air and immiscible fluid segments 42 and 43, respectively, are drawn into probe 46. In this fashion, no extra sample segments are introduced into the system. Appropriate diluent is added to each sample segment before being injected with reagent by an injection mechanism (not shown).

The interdigitated sample segments are flowed as a continuous stream past two reagent injection zones, Zone 1 and Zone 2, by mechanism 57. The reagent is not introduced continuously into the sample stream flowing along conduit 40, as customary in the prior art. Rather, a predetermined controlled volume of reagent is selectively injected, under pressure, into a selected sample segment 41 through the layer of encapsulating immiscible fluid 43. The immiscible fluid 43 is pierced and reforms itself after reagent injection, to maintain sample segment integrity and prevent contamination of a subsequent sample segment 41.

Reagents are selectively injected into each sample segment 41 as the individual sample segments 41 flow past Zones 1 and 2. Each zone comprises a block 99 which defines an inner conduit 40' which connects to outer conduit 40 by appropriate fittings. Inner conduit 40' has a number of reagent injectors 55 located at positions about its periphery, which are more particularly designated 55a–55c and 55d–55g. Each reagent injector, as hereafter further described, is operative to introduce a predetermined volume of one reagent into conduit 40'. For example, injector 55a may contain a reagent for analyzing glucose; injector 55b may contain a reagent for analyzing BUN; injector 55c may contain a reagent for analyzing LDH; etc. If only the three aforementioned tests are desired to be made, then three sample segments 41 are aspirated by probe 46, under the control of controller 58. Each of such sample segments are thereafter injected with a predetermined volume of the appropriate reagents by injectors 55a, 55b, and/or 55c, in any order, under the control of controller 58. Injectors 55 may be arranged in Zones 1 and 2, respectively. Detectors 50 and 51, respectively, sense the leading edge of each air segment 42 entering into Zone 1 and Zone 2, and provide a control signal to controller 58. Alternatively, the leading edge of each liquid segment 41 may provide the control signal to controller 58. The controller 58, after an appropriate delay and in accordance with the information provided from label 54, operates the appropriate one of the reagent injectors 55 to introduce a predetermined volume of a selected reagent into the sample segment 41 following the monitored air segment 42. Reagents are injected into the appropriate sample segment on a controlled selective basis. For example, injector 55a being the first of the injectors 55 may fire 0.5 seconds after a leading edge of an air segment 42 is sensed. If injector 55b is programmed to fire instead, then it may inject after a 0.6 second delay, and similarly injector 55c may introduce reagent after a 0.7 second delay, etc.

The selective injection of reagent may operate in the following manner:

(a) A marker segment, not shown, can be injected periodically into conduit 40, for example, by immersion of the probe 46 into a reservoir containing an aqueous liquid of characteristic optical qualities. The detector 50 senses such marker segment and relays this information to controller 58.

(b) Detector 50 senses the leading edge of each air segment 42 in conventional fashion, separating each sample segment 41, and the controller fires various ones of injectors 55a, 55b, 55c, etc. (each of which contains the appropriate reagents) at the proper time, i.e., when the particular sample segment 41 is opposite or adjacent the appropriate injector 55.

(c) The controller 58 will count each air segment 42, using the marker segment as a control reference, so that it will be able to keep track of each particular sample segment 41. Detection of the periodic passage of marker segments helps the controller 58 to keep track of each particular set of sample segments, as described in the copending Pelavin U.S. patent application, Ser. No. 21,034, filed on Mar. 16, 1979, and assigned to a common assignee. The marker will provide a reference about which each sample set can be located.

After the reagents have been injected into the selected sample segment 41, the sample and reagents are reacted as they flow in a segmented pattern towards the analyzing station 56 located downstream from the reagent injection Zones 1 and 2. The analyzing station detects the reaction of the sample reagents to quantitatively determine the desired analyte in the sample.

The analyzing station 56 may comprise a colorimeter (not shown) or other detector that optically analyzes each reaction at an appropriate wavelength. The controller 58 adjusts the colorimeter to the appropriate wavelength setting for each particular reacted sample segment. The detector 52 senses the leading edge of each air segment 42 between each reacted sample segment, and the controller 58 adjusts the colorimeter after computing an appropriate delay. Alternatively, the control signal may be derived "on line" from an IR detector (similar to detector 52) located at the colorimeter flow cell. The controller 58 again counts the air segments 42, and senses appropriate marker segments to keep track of each particular sample segment within each set of sample segments, respectively.

The inventive analyzing system of FIG. 2 depicts two reagent injection Zones 1 and 2, but a single zone can be provided, if injectors 55 can be conveniently accommodated within the space allocated for injection. Also, more than two reagent zones may be needed to effect a large plurality of chemistries. In certain cases, three or more reagents may have to be injected, each requiring an extended incubation between a subsequent reagent injection. Hence, there may be required multiple spaced-apart injection zones.

Reagent introduction causes the sample segment to elongate within conduit 40', which elongation will cause timing and flow changes with downstream reagent introduction and analyses. Therefore, it is preferable to locate all the injectors 55 compactly, e.g., circumferentially about the axis of conduit 40 at each injection location, as illustrated in FIGS. 3 and 4–6. Zones 1 and 2 illustrate seven reagent injection locations having three injectors each, for a total of twenty-one discrete reagent injectors 55. Thus, as herein shown, it is contemplated to inject any selected sample segment with any one or more of twenty-one different reagents.

Sample segments injected with reagent in Zone 1 may also require a second injection of another reagent in Zone 2. Having been injected with reagent in Zone 1, the sample segment will be elongated, but the timing of the second injection will be maintained due to detector 51. Detector 51 will sense the leading edge of the corresponding air segment 42 associated with the respective injected sample segment as it approaches Zone 2. Detector 51 will inform the controller 58 of the sample segment 41 approach, and controller 58 will initiate the second injection with the required delay. A third zone, if necessary, would have a similar structural requirement.

In order to provide a compact flow stream, minimize flow changes, and to conserve on reagent materials, it is also contemplated to use minute volumes of reagent, i.e., generally but not limited to 5 to 15% reagent per volume of sample including diluent.

Figure 5:
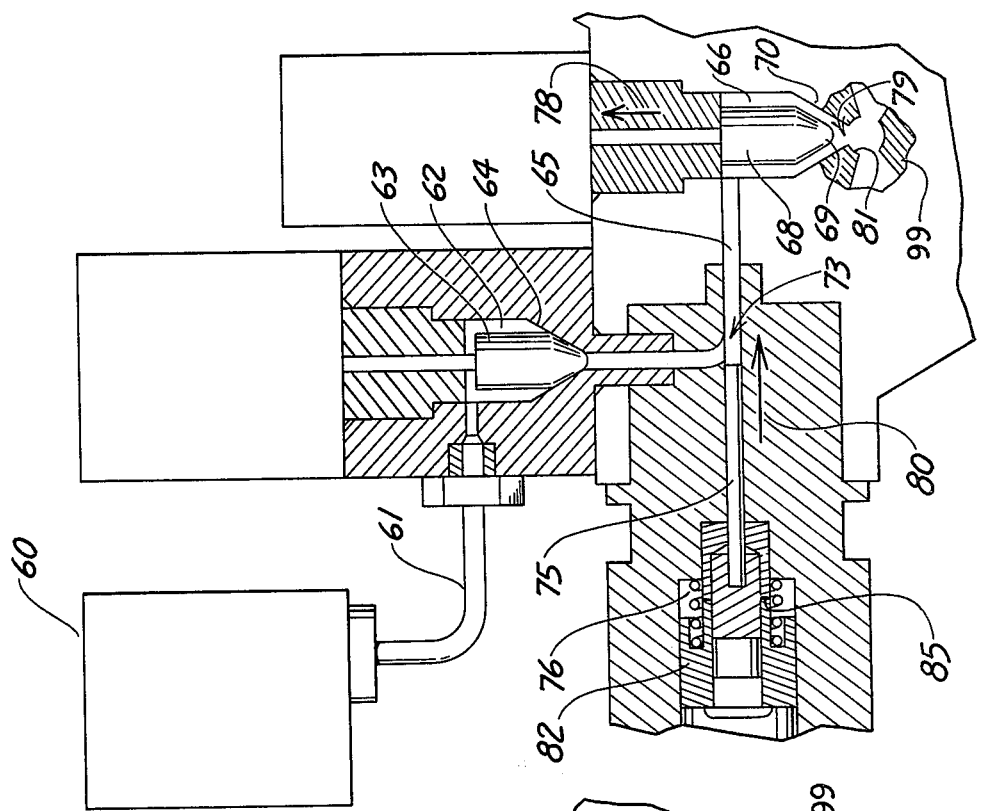
Figure 6:
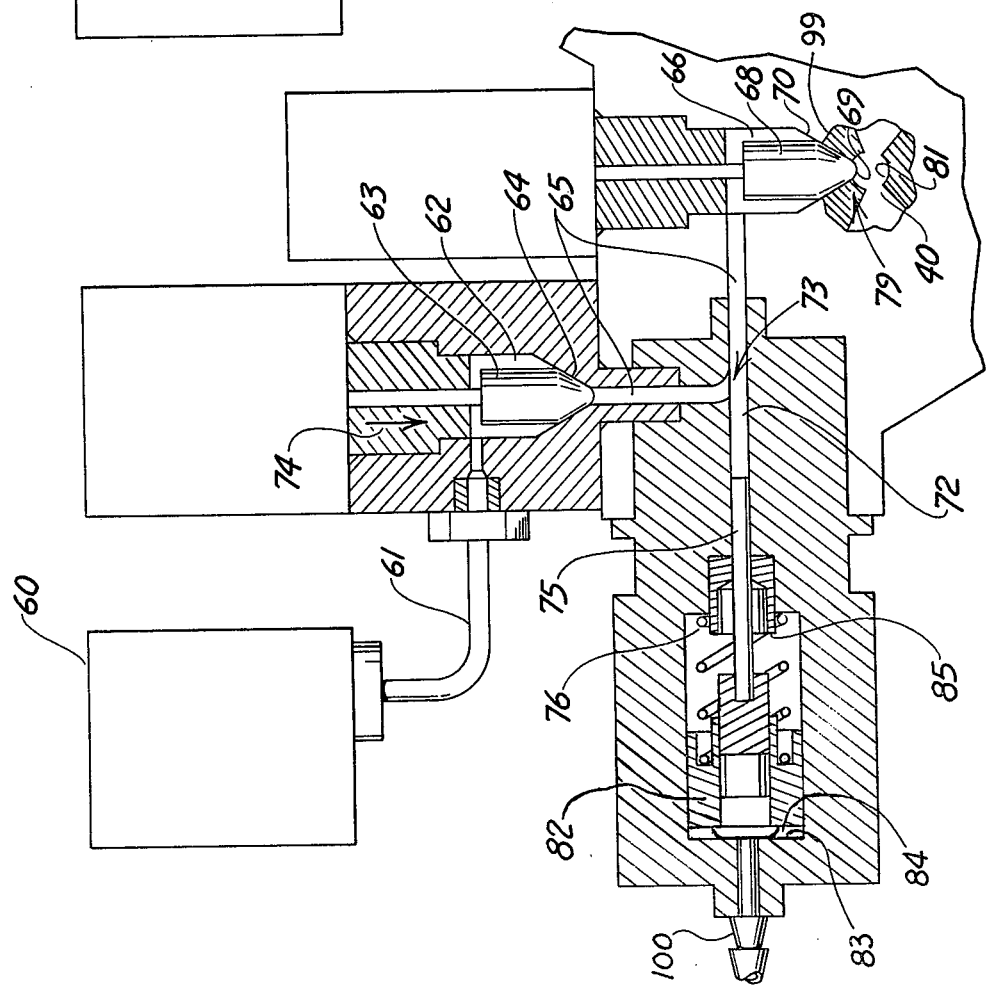

Now referring to FIGS. 4 through 6, an embodiment of a reagent injector apparatus for each injector 55 of FIG. 2 is illustrated. The particular reagent is stored in a reservoir 60 which feeds to chamber 62 via conduit 61. Chamber 62 has a poppet valve 63 which seals against the seat 64 of chamber 62. When the poppet valve 63 is withdrawn from the seat 64, as depicted by arrow 67 in FIG. 4, chamber 62 in fluid communication with chamber 66 via conduit 65. Chamber 66 contains a poppet valve 68 which seals against seat 70 of chamber 66. A tip 69 of the poppet valve 68 projects through an aperture 79 in conduit 40' of the analyzing system of FIG. 2. The tip 69 of the poppet valve can be convex, as shown, or it may also be flush with the inner wall 81 of the conduit 40'.

While poppet 63 is withdrawn (arrow 67), hydraulic pressure is released in cavity 84 and a ram or piston 75 in conduit 72 is withdrawn (arrow 71) by action of spring 76 driving piston 82 against abutment 83. On the forward stroke, the piston 82 comes to rest against abutment 85, thus defining the throw distance of ram 75. Conduit 72 connects with conduit 65 at the elbow junction 73. Conduit 72 will fill with reagent from reservoir 60 to the end of the ram 75. The abutment 83 is adjustable to change the throw distance of ram 75 which determines the volume of the aliquot of reagent injected into conduit 40' from conduit 72.

After piston 82 is firmly abutted against abutment 83, the poppet valve 63 is subsequently seated against seat 64 (arrow 74), as shown in FIG. 5. The injection apparatus is now primed to inject a predetermined amount or aliquot of reagent from the conduit 72.

When the selected sample segment 41 to be injected flows past the injector 55, the poppet valve 68 is withdrawn from seat 70 as depicted by arrow 78 in FIG. 6. The ram 75 is forced forward (arrow 80) in conduit 72 against the biasing influence of the spring 76 by hydraulic pressure applied at port 100. In so doing, a given amount of reagent is injected under pressure to the sample segment 41 in the conduit 40'. The immiscible fluid 43 is pierced by the pressurized reagent, and the sample segment swells to a new volume within conduit 40'.

The apparatus depicted in FIGS. 4 through 6 is a primed injection device, that can quickly inject an aliquot of reagent into the sample segment on command from controller 58 (FIG. 2). The throw distance and diameter of ram 75 determines the amount of reagent which will fill conduit 72, and, hence, be injected into the sample segment 41 upon the sealing of poppet 63.

The tip 69 of the poppet valve plays a very important role in the injection of the reagent into the sample segment. Tip 69, preferably, is of similar material as the conduit 40', so that the immiscible fluid 43 also, preferentially, wets tip 69. In effect, tip 69 is designed to be part of the conduit wall 81, so as to maintain proper flow of immiscible fluid 43 over the inner wall surface of conduit 40' and accelerate reforming of the layer of immiscible fluid 43 pierced by the reagent around the sample segment. In addition, the tip 69 is designed to be flush or slightly convex with the inner wall 81 of conduit 40', so that fluids, e.g., reagents, are not trapped in any concave depression which might be formed in wall 81 of conduit 40'.

It is very important that the fluid dynamics of the piercing and the reforming of the immiscible fluid layer be properly achieved, so that each sample segment remains encapsulated in a protective sheath of immiscible fluid both before and after injection. This is necessary, as aforementioned, in order to maintain sample integrity and to prevent contamination of carryover between successive sample segments 41.

For purposes of this invention, the immiscible fluid 43 can be a fluorocarbon oil, and both the conduit wall 81 and the poppet valve tip 69 can be a Teflon material. The fluorocarbon oil will preferentially wet the wall 81 and tip 69 surfaces to the exclusion of the aqueous sample fluid.

Having thus described the invention, what is desired to be protected by Letters Patent is presented by the following appended claims.

What is claimed is:

1. A continuous system for analyzing a number of liquid samples, comprising:
   a conduit defining a sample flow path;
   means for conveying said liquid samples successively as sets of discrete sample segments and as a continuous stream along said flow path;
   means disposed along said flow path for selectively introducing, in a variable controlled sequence, precise aliquots of different reagents into select ones of said sample segments in each of said sets to react said selected sample segments each in respect of at least a particular analyte;
   means for controlling the sequence in which said various reagent aliquots are introduced into each of said sets; and
   means disposed along said flow path for analyzing said samples.

2. The system of claim 1, further comprising means disposed along said flow path for detecting the flow of said sample segments along said flow path, said control means being responsive to said detecting means.

3. The system of claim 1, further comprising means for introducing said discrete sample segments along said flow path, and means associated with said sample introducing means for indicating the different analyses to be effected in respect of sample segments in each of said sets, said controlling means being responsive to said indicating means.

4. The system of claim 3, wherein said sample introducing means is operative to segment each liquid sample to define a set equal to the number of different analytes to be determined in respect of said each liquid sample.

5. The system of claim 3, wherein said sample introducing means comprises means for aspirating said successive sample segments, each separated by at least an inert fluid segment.

6. The system of claim 3, wherein said sample introducing means comprises means for introducing an immiscible fluid along said flow path, said immiscible fluid preferentially wetting the surfaces of said conduit to the exclusion of said sample segments.

7. The system of claim 3, wherein said indicating means further comprises means for reading a label associated with each sample set.

8. The system of claim 7, wherein each label comprises a code for indicating the different analyses to be performed for each respective sample set.

9. The system of claim 1, wherein said reagent introducing means introduces aliquots of reagents which are generally but not limited to between 5% and 15% by volume of the sample segments inclusive of diluent.

10. The system of claim 1, wherein said sample analyzing means comprises a colorimeter.

11. The system of claim 10, further comprising means responsive to said detecting means for changing the operating wavelength of said colorimeter in respect of each sample segment, so as to correspond with the analyte to be analyzed in said each sample segment.

12. The system of claim 1, further comprising means for introducing a marker into said flow path in order to monitor the number of sample sets being conveyed along said flow path.

13. The system of claim 12, further comprising means disposed along said flow path for detecting said marker.

14. A method for quantitatively determining analytes in discrete liquid samples, said method comprising the steps of:
(a) flowing said liquid samples successively as a continuous stream through said conduit;
(b) dividing each of said liquid samples into a number of discrete segments equal, at least, to the number of analytes to be determined;
(c) introducing a controlled quantity of at least one reagent of a plurality of reagents into each of said sample segments in each of said sets on a selective basis to react said sample segments in each of said sets in respect of said different analytes; and
(d) analyzing said reacted sample segments in each of said sets in respect of said different analytes.

15. The method of claim 14, comprising the further step of separating successive ones of said sample segments by at least an inert fluid segment.

16. The method of claim 14, comprising the further step of introducing said reagent as said sample segments are flowed along said conduit.

17. The method of claim 14, comprising the further step of introducing two or more of said plurality of reagents in a plane or planes transverse of said conduit.

18. The method of claim 14, comprising the further step of introducing two or more of said plurality of reagents at separate points along said conduit.

19. The method of claim 14, comprising the further step of introducing an immiscible fluid to preferentially wet the surfaces of said conduit to the exclusion of said sample segments.

20. The method of claim 15, comprising the further step of introducing an immiscible fluid to preferentially wet the surfaces of said conduit to the exclusion of said sample segments and said inert fluid segments.

21. The method of claim 14, comprising the further steps of identifying the analytes to be determined in respect of each of said liquid samples, and controlling the introduction of said controlled quantity of reagents into said sample segments according to said analytes to be determined.

22. The method of claim 14, comprising the further steps of identifying the analytes to be determined in respect of each of said liquid samples, each of said liquid samples being divided into a number of sample segments, so as to define a set, equal to said number of analytes to be determined.

23. Apparatus for quantitatively determining one or more analytes in a plurality of discrete samples, comprising:
a conduit;
means for dividing said samples into sets of discrete sample segments;
means for flowing said sets of discrete sample segments successively as a continuous stream through said conduit, said successive sample segments being separated by at least an inert fluid segment;
a reagent injection station disposed along a portion of said conduit, said injection station including means to introduce, on a selective basis, aliquots of reagents into sample segments passing along said conduit portion;
means for controlling said injection station, on a selective basis, to introduce selected reagents into said conduit portion, to mix with a particular one of said sample segments; and
an analyzing station disposed downstream of said injection station for analyzing said sample segments.

24. The apparatus of claim 23, including means for introducing an immiscible fluid along said conduits, said immiscible fluid preferentially wetting the surfaces of said conduit to the exclusion of said sample segments.

25. The method of claim 23, comprising the further step of introducing an immiscible fluid to preferentially wet the surfaces of said conduit to the exclusion of said sample segments and said inert fluid segments.

26. The apparatus of claim 23, further comprising detection means disposed along said conduit for locating sample segments to be injected with reagent.

27. The apparatus of claim 23, wherein said reagent station comprises a plurality of poppet valves disposed about said conduit, each of said valves having a tip which forms part of the conduit wall.

28. The apparatus of claim 27, wherein each of said tips is substantially flush or slightly convex with respect to said conduit wall.

29. The apparatus of claim 27, wherein said plurality of valves are disposed circumferentially about said conduit.

30. The apparatus of claim 23, wherein said tips of said poppet valves are comprised of the same material as said conduit wall.

31. The apparatus of claim 30, further including means for introducing an immiscible fluid along said conduit, said immiscible fluid preferentially wetting the surfaces of said conduit and the tips of said poppet valves to the exclusion of said sample segments.

* * * * *